US011497386B2

(12) United States Patent
Do (10) Patent No.: US 11,497,386 B2
(45) Date of Patent: Nov. 15, 2022

(54) CONTROL ELEMENT FOR AN ENDOSCOPIC APPARATUS, AND ENDOSCOPIC APPARATUS COMPRISING A CONTROL ELEMENT OF THIS KIND

(71) Applicant: HOYA CORPORATION, Tokyo (JP)

(72) Inventor: Anh Minh Do, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 230 days.

(21) Appl. No.: 16/633,841

(22) PCT Filed: Jul. 24, 2018

(86) PCT No.: PCT/IB2018/000765
§ 371 (c)(1),
(2) Date: Jan. 24, 2020

(87) PCT Pub. No.: WO2019/021052
PCT Pub. Date: Jan. 31, 2019

(65) Prior Publication Data
US 2021/0000328 A1 Jan. 7, 2021

(30) Foreign Application Priority Data
Jul. 25, 2017 (DE) .......................... 102017116761.7
Jul. 25, 2017 (DE) .......................... 102017116762.5

(51) Int. Cl.
*A61B 1/00* (2006.01)
*A61B 1/005* (2006.01)

(52) U.S. Cl.
CPC .......... *A61B 1/0057* (2013.01); *A61B 1/0052* (2013.01); *A61B 1/00133* (2013.01)

(58) Field of Classification Search
CPC .. A61B 1/0057; A61B 1/0052; A61B 1/00133
See application file for complete search history.

(56) References Cited

U.S. PATENT DOCUMENTS 4,256,113 A * 3/1981 Chamness ............... A61B 18/14
606/47
5,254,088 A 10/1993 Lundquist et al.
(Continued)

FOREIGN PATENT DOCUMENTS

| JP | H02-46820 A | 2/1990 |
| JP | H02-161928 A | 6/1990 |
| JP | H04-82529 A | 3/1992 |

OTHER PUBLICATIONS

International Search Report dated Nov. 29, 2018 filed in PCT/IB2018/000765.
(Continued)

*Primary Examiner* — Alexandra L Newton
*Assistant Examiner* — Rynae E Boler
(74) *Attorney, Agent, or Firm* — Greenblum & Bernstein, P.L.C.

(57) ABSTRACT

The invention relates to a control element for an endoscopic device (A) with a retainer; at least one control wire, which can be moved back and forth in the longitudinal direction of the wire, for control purposes on the endoscopic device (A); a control wire tensioning element guided in the retainer, wherein the control wire is mounted in the control wire tensioning element; and a displacement force application device supported on the retainer, by means of the displacement force application device the control wire tensioning element can be moved relative to the retainer, in order to effect fine adjustment of the control wire.

The invention further relates to a control element for an endoscopic device (A), having a housing element with a guide; at least one control wire for control purposes with the endoscopic device (A); a lever element, which can be displaced in the longitudinal direction of the housing element on the guide of the housing element, with the at least one control wire being anchored on the lever element. The (Continued)

anchoring location of the control wire in the lever element is eccentric to the displacement path of the lever element on the guide of the housing element.

11 Claims, 10 Drawing Sheets

(56) References Cited

U.S. PATENT DOCUMENTS

| | | | | |
|---|---|---|---|---|
| 5,376,094 A * | 12/1994 | Kline | ............... | A61B 17/221 |
| | | | | 606/110 |
| 5,810,715 A | 9/1998 | Moriyama | | |
| 6,258,101 B1 * | 7/2001 | Blake, III | ............ | A61B 17/221 |
| | | | | 606/113 |
| 2005/0272975 A1 * | 12/2005 | McWeeney | ........ | A61B 1/00103 |
| | | | | 600/113 |
| 2007/0106304 A1 * | 5/2007 | Hammack | .......... | A61B 17/8014 |
| | | | | 606/113 |
| 2011/0207999 A1 * | 8/2011 | Torisawa | .......... | A61M 25/0136 |
| | | | | 600/114 |

OTHER PUBLICATIONS

Office Action issued in Japanese Counterpart Patent Appl. No. 2020-500852, dated Jul. 19, 2020.

* cited by examiner

CONTROL ELEMENT FOR AN ENDOSCOPIC APPARATUS, AND ENDOSCOPIC APPARATUS COMPRISING A CONTROL ELEMENT OF THIS KIND

TECHNICAL FIELD

The present invention relates to a control element for an endoscopic device and further to an endoscopic device with such a control element.

More precisely, the present invention relates to a control element with a retainer and at least one control wire for control purposes on the endoscopic device, it being possible to move the control wire back and forth in the retainer in the longitudinal direction of the wire.

BACKGROUND ART

Such a control element can be used with a plurality of endoscopic devices in which a control wire is moved back and forth in the longitudinal direction of the wire.

For example, such a control element is used with a flexible endoscope having a bending section, wherein a control wire is anchored on the distal end of the bending section such that the anchoring location is spaced apart from the center line of the endoscope. The control wire extends through the bending section to a control element arranged on the proximal side of the endoscope. Thus, the control element is actuated from the proximal side. Due to actuation of the control element, the control wire is tensioned, whereby the bending section is bent.

In use, the most precise bending possible of the bending section is desired. This means that the user should be capable of achieving the targeted bending of the bending section as precisely as possible by means of actuating the control element.

SUMMARY OF INVENTION

Technical Problem

Thus, the object of the invention is to obtain a control element for an endoscopic device and an endoscopic device having such a control element, via said endoscopic device an exact bending of the bending section is executed by means of a simple operation.

Solution to Problem

In a first aspect, this object is achieved by a control element having the features of claim 1.

With respect to the endoscopic device, the object is achieved by an endoscopic device having the features of claim 11.

Advantageous further developments are the subject matter of the dependent claims.

In the first aspect, the control element for an endoscopic device has a retainer; at least one control wire, which can be moved back and forth in the longitudinal direction of the wire, for control purposes on the endoscopic device; a control wire tensioning element guided in the retainer, wherein the control wire is mounted in the control wire tensioning element; and a displacement force application device supported on the retainer, by means of said displacement force application device the control wire tensioning element can be moved relative to the retainer, in order to effect fine adjustment of the control wire.

By means of the displacement force application device, the control wire tensioning element can be moved relative to the retainer. Thus, the control wire mounted in the control wire tensioning element can be specifically finely controlled through simple actuation of the control wire tensioning element.

The retainer may have a rail; the control wire tensioning element may have a groove, which extends in the longitudinal direction of the control wire tensioning element; and the control wire tensioning element can be displaced along the retainer due to engagement of the rail in the groove. Due to the displacement of the control wire tensioning element along the retainer, the control wire can be shifted directly in its longitudinal direction.

The displacement force application device may be designed as a control wheel with an inner thread, wherein the inner thread of the control wheel has thread engagement with an outer thread of the control wire tensioning element such that the control wire tensioning element can be moved relative to the retainer. A simple and direct transfer of force from the control wheel to the control wire tensioning element is thereby implemented. A shifting movement of the control wire is implemented by means of a rotational movement occurring on the control wheel. A gear ratio of the rotational movement to be applied at the control wheel for the resulting displacement path of the control wire is established in a simple manner with this design. An especially advantageous fine adjustment of the displacement path of the control wire is thereby enabled.

The control wheel may have knurling on the outer circumferential surface. The actuation of the control wheel is thereby simple and easy. The rotation of a control wheel provided with knurling is familiar to users. The knurling can be moved and simultaneously securely retained with a finger. Unintentional faulty actuation can thereby be limited.

The displacement force application device may be designed as an electric motor or as a piezo element. Motorized adjustment of the displacement path of the control wire can thereby be implemented. An even more exact fine adjustment of the displacement path of the control wire is thereby enabled.

The control wire tensioning element may be designed as a screw with a cavity, wherein a control wire nipple for the at least one control wire is mounted in the cavity. The control wire can be easily dismantled.

An eyelet may be formed on the proximal side of the retainer, into said eyelet a finger or thumb can be inserted. The user can thereby securely grasp the retainer and move the control wire back and forth in a targeted and controlled manner by placing the thumb and one finger in the eyelet and on the control wheel.

A proximal end of the at least one control wire may be mounted in the control wire tensioning element.

The control element may have an angled wire guide element, on which the control wire is guided to the control element such that it changes its direction. Thus, the control element extends away from an endoscope, to which it is connected. The user can thereby securely grasp the retainer without other elements, e.g. of an endoscope, being in the way.

The endoscopic device is equipped with a previously described control element.

The endoscopic device may be a flexible endoscope.

Alternatively, the endoscopic device may be a rigid endoscope.

The control element according to the invention can be used with any type of endoscope, which uses a control wire to control an element to be controlled.

In a second aspect, the object is achieved by a control element having the features of claim 12.

With respect to the endoscopic device, the object is achieved by an endoscopic device having the features of claim 22.

Advantageous further developments are the subject matter of the dependent claims.

In the second aspect, the control element for an endoscopic device has a housing element with a guide; at least one control wire for control purposes with the endoscopic device; and a lever element, which can be displaced in the longitudinal direction of the housing element on the guide of the housing element, with the at least one control wire being anchored on the lever element; wherein the anchoring location of the control wire in the lever element is eccentric to the displacement path of the lever element on the guide of the housing element.

Thus, a control element is obtained, which can specifically tension the control wire in the longitudinal direction of the housing element. A very exact and fine tensioning of the control wire is enabled.

The lever element may be pivotable relative to the housing element.

The lever element may be rotatable about a pivot point relative to the housing element, said pivot point being situated on the displacement path of the lever element on the guide of the housing element.

In this case, a control element is obtained that not only can tension the control wire specifically in the longitudinal direction of the housing element but that can provide further tensioning, in addition, by means of a pivot movement of the lever element. An even more precise control is achieved during tensioning of the control wire.

The lever element may have two anchoring locations for each control wire, and the two anchoring locations may be spaced apart, at an equal distance to one another, from the displacement path of the lever element on the guide of the housing element. Thus, two control wires can simultaneously be tensioned and/or relaxed by a single movement of the lever element. The strength of the tensioning of the one wire and the strength of the relaxing of the other wire are equal in this case.

The lever element may have two anchoring locations for each control wire, and the two anchoring locations may be spaced apart, at an unequal distance to one another, from the displacement path of the lever element on the guide of the housing element. Thus, two control wires can simultaneously be tensioned and/or relaxed by a single movement of the lever element. The strength of the tensioning of the one wire and the strength of the relaxing of the other wire, however, are different in this case.

The lever element may have a ring section on an end section of the lever element. The user can thereby securely grasp the end section of the lever element and move the control wire back and forth in a targeted and controlled manner due to insertion of a finger in the ring section.

The ring section may be arranged adjacent to the anchoring location of the control wire. The assembled size of the entire control element is thereby kept small.

A ring section may be arranged on the housing element on an end section of the housing element, said section being situated on the opposite side of the housing element for connecting to the endoscopic device. The user can securely retain the housing element by inserting the thumb into said ring section.

The lever element may extend vertically with respect to the extension of the housing element, and the pivot point of the lever element may be arranged in the center of the lever element with reference to the longitudinal direction of the lever element. This provides the user with a control element that is clear and easy to handle, which can finely control the control wire or the control wires in a versatile manner.

The pivot point of the lever element may be arranged at the center of gravity of the lever element.

The endoscopic device is equipped with a previously described control element.

The endoscopic device may be a flexible endoscope.

Alternatively, the endoscopic device may be a rigid endoscope.

The control element according to the invention can be used with any type of endoscope, which uses a control wire to control an element to be controlled.

The previously explained aspects of the present invention may be suitably combined.

DESCRIPTION OF EMBODIMENTS

The present invention is described in more detail in the following by means of exemplary embodiments with reference to the drawings.

First Exemplary Embodiment

A first exemplary embodiment of the present invention is described with reference to FIGS. 1 to 9 in the following.

Figure 1:
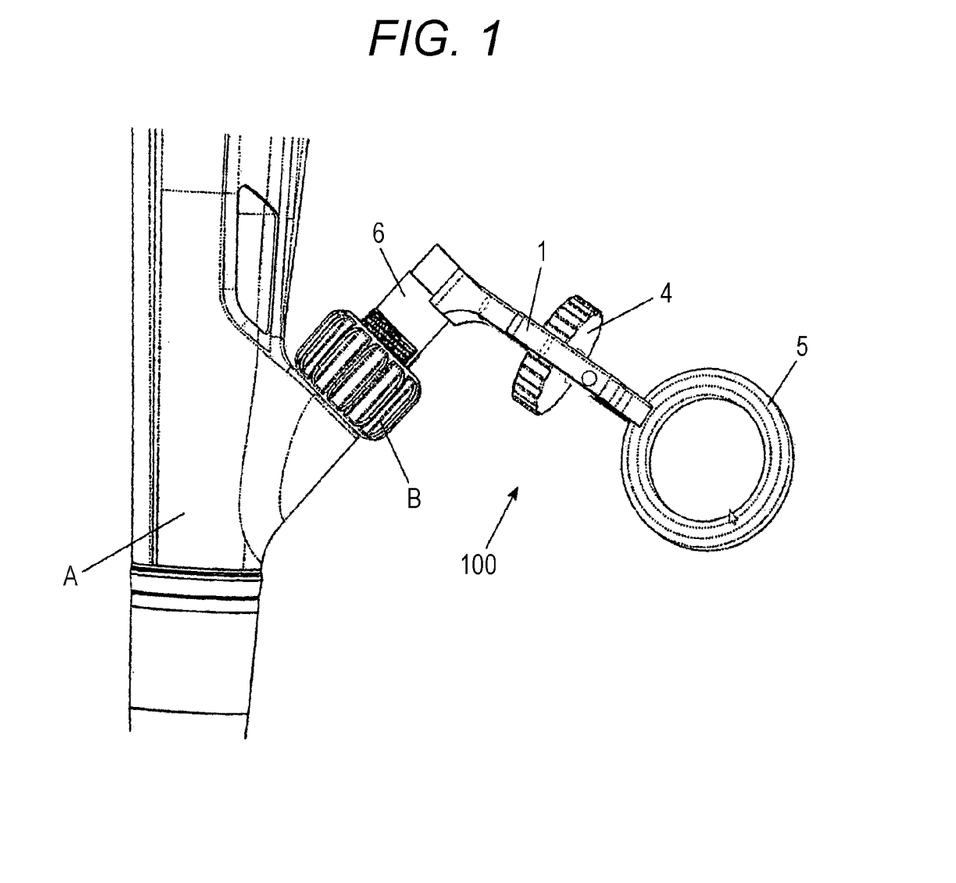
FIG. 1 shows a schematic perspective view of a control element, connected to an endoscope, of an exemplary embodiment of the present invention.

A control element 100 according to the invention is coupled to an endoscope A, e.g. via a screw connection B, which is provided on the endoscope A at the connection location of the control element 100.

To this end, the control element 100 is used to tension and to relax a control wire 2 in the longitudinal direction of the wire in order to control a working element, which is provided on the distal side of the control wire 2.

Merely as an example, the control element 100 may be used with a flexible endoscope A having a bending section. In this case, the control wire 2 is anchored on the distal end of the bending section such that the anchoring location is spaced apart from the center line of the endoscope tube. The control wire 2 extends through the bending section to a control element 100 arranged on the proximal side of the endoscope A. Thus, the control element 100 is actuated from the proximal side. Due to actuation of the control element 100, the control wire 2 is tensioned, whereby the bending section is bent.

The precise structure and function of the control element 100 are described in the following.

Figure 2:
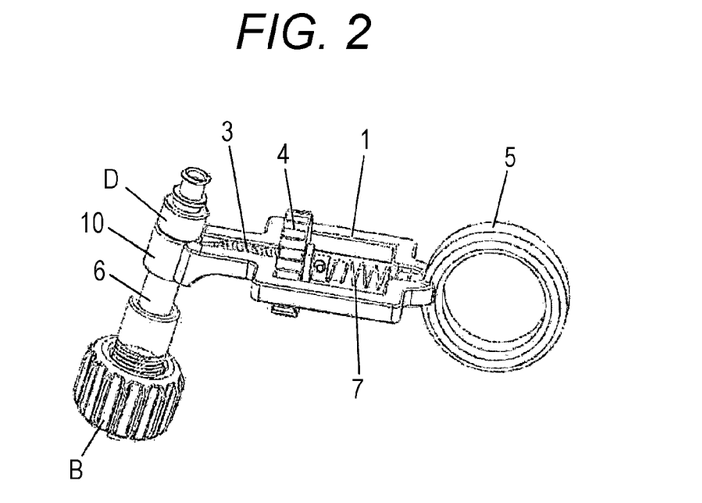
FIG. 2 shows a schematic perspective view of the control element from FIG. 1.

The control element 100 has a housing, which acts as a retainer 1. A wire guide element 6 extends away from the endoscope A from the connection B on the endoscope A in a proximal direction. The wire guide element 6 is designed as a tube. The control wire 2 is guided in the wire guide element 6. The wire guide element 6 has, at a suitable location, a wire outlet opening, at which the control wire 2 can exit the wire guide element 6, e.g. laterally or alternatively (not shown) in the axial direction of the wire guide element 6. A connection element 10 of the retainer 1 encloses the wire guide element 6 in the region of the wire outlet opening. The connection element 10 is formed on the retainer 1 and is used for suitable attachment of the retainer 1 to the wire guide element 6. The connection element 10 may be detachable from the wire guide element 6 in order to remove the retainer 1 from the wire guide element 6 as needed. The retainer 1 has a longitudinal extension. The connection element 10 is designed such that the control wire 2 can move from the wire outlet opening of the wire guide element 6 in the direction of the longitudinal extension of the retainer 1.

The wire guide element 6 functions as a spacing element in order to suitably space the control element 100 apart from the endoscope A. This can improve the handling of the control element 100, because it is easier to grasp the control element 100 without elements of the endoscope A being in the way.

The control wire 2 extends, in the interior of the wire guide element 6, to the retainer 1 in the proximal direction such that it changes its direction. The wire guide element 6 thereby acts as an angled wire guide element, on which the control wire 2 is guided to the retainer 1 such that it changes its direction.

An adapter D may be provided on the end of the wire guide element 6 opposite the connection B. Further devices usable on the endoscope A may be connected on the adapter D as needed, such as a baby scope, a micro-tool connection, a rinsing connection for rinsing water, a suction connection for suctioning of fluids, etc.

The connection element 10 is arranged between the connection B and the adapter D.

Figure 3:
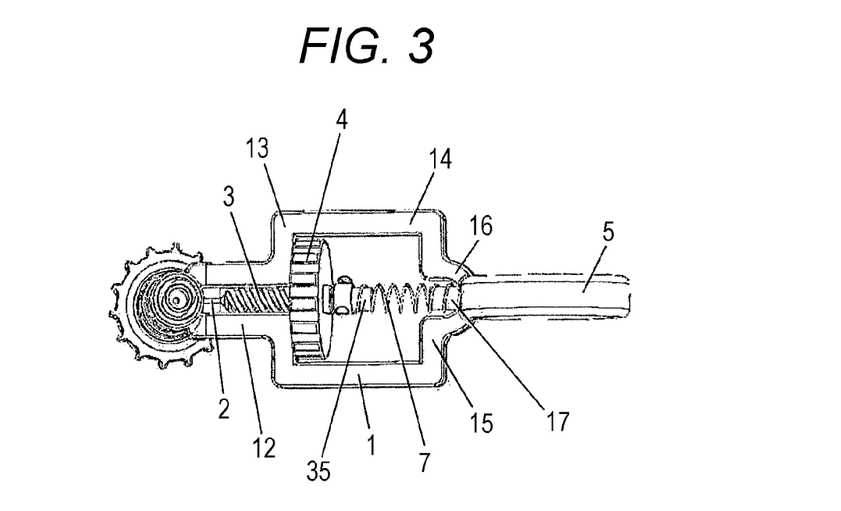
FIG. 3 shows a schematic perspective view of the control element from above.
Figure 4:
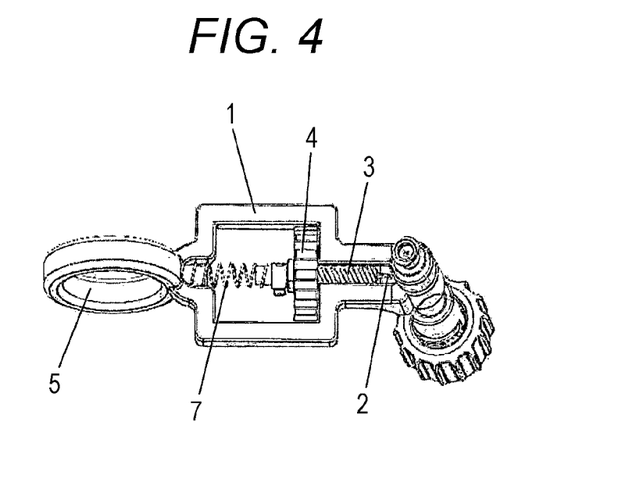
FIG. 4 shows a schematic perspective view of the control element from below.
Figure 5:
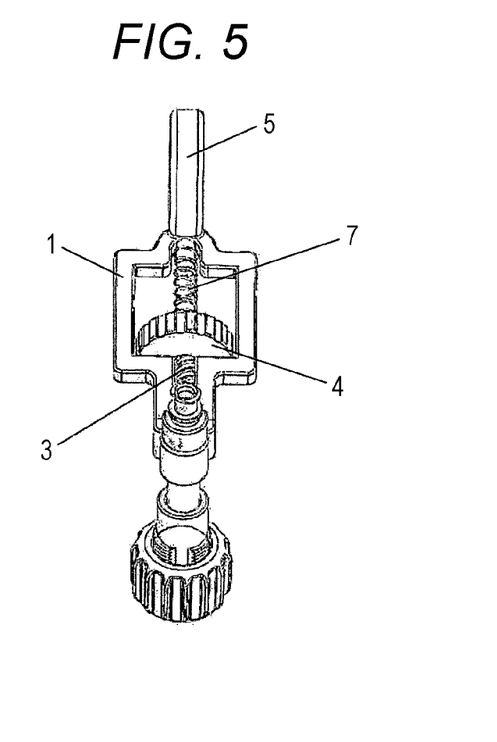
FIG. 5 shows a further schematic perspective view of the control element from below.
Figure 6:
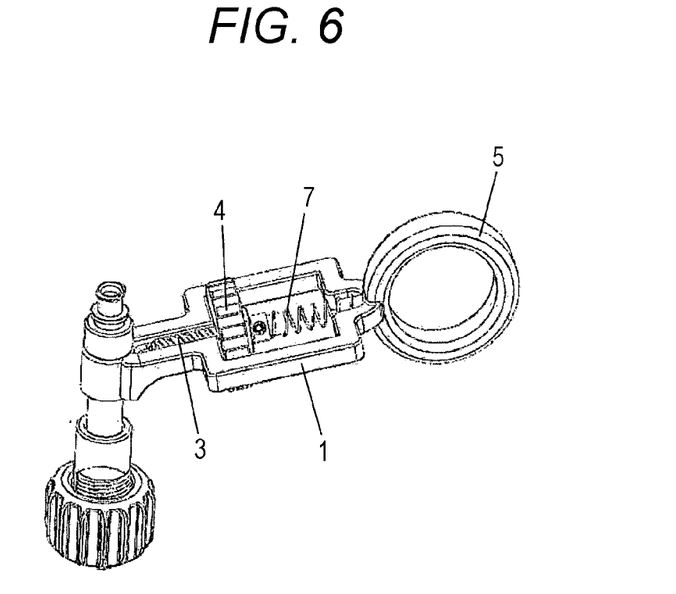
FIG. 6 shows a schematic perspective view of the control element.
Figure 7:
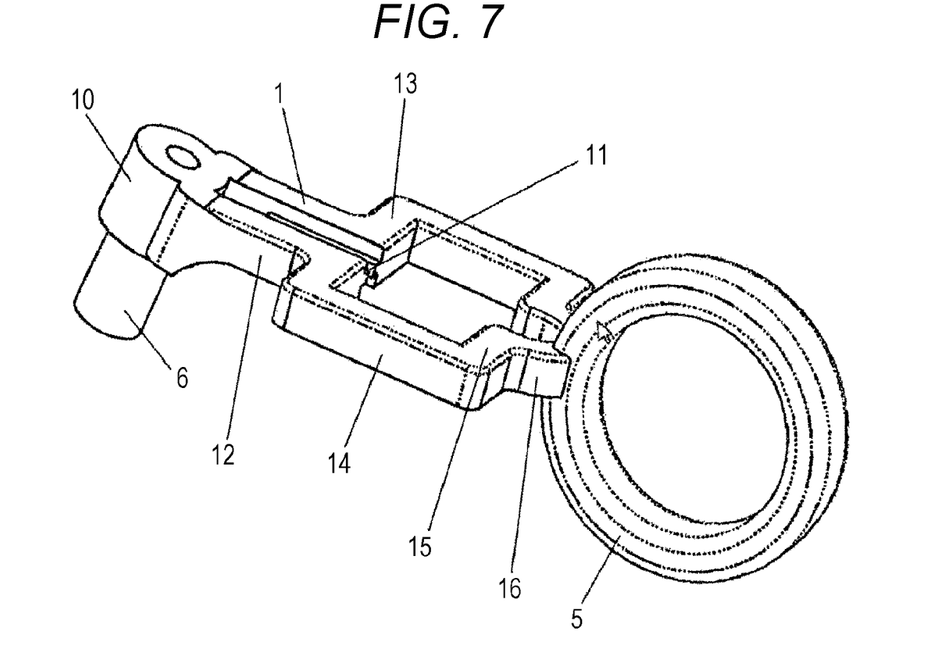
FIG. 7 shows a schematic perspective view of the more detailed structure of the control element.

The retainer 1 forms an axial-symmetrical frame element, as is shown in FIGS. 3 and 7. More precisely, the retainer 1 is arranged in a mirror image about its axis of longitudinal extension. Two parallel first axial braces 12 extend from the connection element 10 in the axial direction of the retainer 1. At the end of the axial braces 12 opposite the connection element 10, respective first radial braces 13 extend away from the longitudinal axis of the retainer 1 at a right angle. At the end of the first radial brace 13 opposite the longitudinal axis of the retainer 1, respective second axial braces 14 extend parallel to the longitudinal axis of the retainer 1. At the end of the second axial braces 14 opposite the first radial braces 13, respective second radial braces 15 extend toward the longitudinal axis of the retainer 1 at a right angle. At the end of the second radial brace 15 opposite the second axial braces 14, respective axial end braces 16 extend parallel to the longitudinal axis of the retainer 1. An eyelet 5 is provided on the side of the axial end braces 16 opposite the second radial braces 15.

The retainer 1 may be produced from plastic or metal.

A rail 11 is provided on the side of the first axial braces 12 pointing toward the center axis or longitudinal axis; see FIG. 7. The rails 11 of the two first axial braces 12 are parallel to one another and facing one another.

The rails 11 guide a control wire tensioning element 3. The control wire tensioning element 3 is more clearly shown in FIG. 9. The control wire tensioning element 3 is a cylindrical element with two parallel grooves 31, which are formed in the longitudinal direction of the control wire tensioning element 3 on the outer circumference of the control wire tensioning element 3 such that they are open in directions opposite one another. The control wire tensioning element 3 is guided by the first axial braces 12 such that one of the grooves 31 slides along one of the rails 11.

Figure 9:
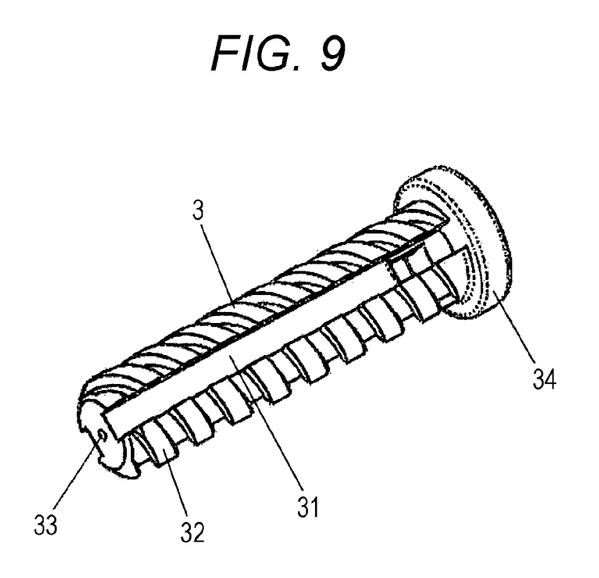
FIG. 9 shows a schematic perspective view of a control wire tensioning element of the control element.

An outer thread 32 is further provided on the outer circumference of the control wire tensioning element 3. The control wire tensioning element 3 is hollow on the inside and has a central hole 33 on the distal end side. A placement ring 34 is provided on the proximal end side. Thus, the control wire tensioning element 3 is designed as a screw with a cavity. A control wire nipple for the control wire 2 is mounted in the interior cavity of the control wire tensioning element 3 such that the control wire 2 extends through the central hole 33 in the distal direction. The control wire nipple forms the proximal end of the control wire 2.

Thus, the control wire 2 extends from the wire outlet opening of the wire guide element 6 into the inner region of the control wire tensioning element 3 and is anchored there.

The control wire tensioning element 3 is embedded in a displacement force application device formed as a control wheel 4 so as to be relatively displaceable.

Figure 8:
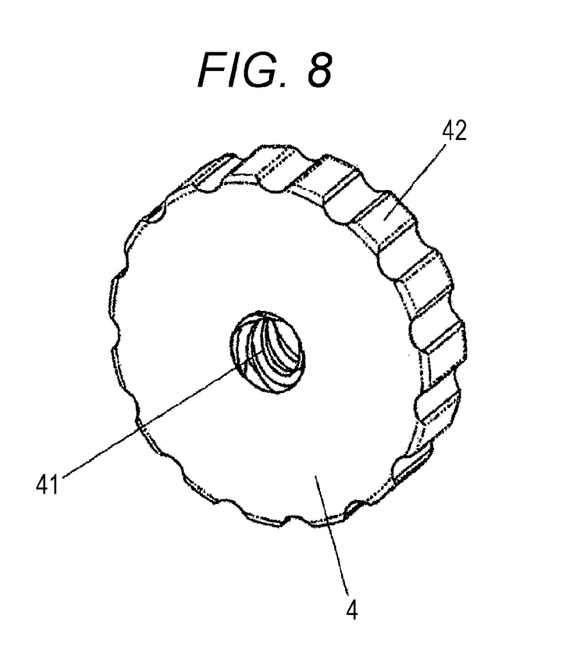
FIG. 8 shows a schematic perspective view of a control wheel of the control element.

The control wheel 4 is shown in FIG. 8 and is formed as a disc-like wheel. The control wheel 4 has a central passage opening, in the inner circumference of which an inner thread 41 is formed. The inner thread 41 has threaded engagement with an outer thread 32 of the control wire tensioning element 3. In other words, the control wire tensioning element 3 (screw) is screwed into the control wheel 4. The control wire tensioning element 3 can be screwed into the control wheel 4 until the front, i.e. the distal, surface of the placement ring 34 is positioned on the proximal end side of the control wire tensioning element 3 on the proximal surface of the control wheel 4.

The control wheel 4 has knurling 42 on its inner circumference, said knurling made up of recesses and protrusions, which enable easy grasping and actuation (rotation) of the control wheel 4.

The control wheel 4 is positioned in the retaining element 1 in the open space, which results from the interior, which is limited by the first radial braces 13, the second axial braces 14, and the second radial braces 15; see FIGS. 2 and 3. In doing so, the front side, i.e. the distal side of the control wheel 4, lies on the proximal side of the first radial brace 13.

On the retaining element 1, a distal protrusion 17 protrudes into the interior in the region of the inner ends of the axial end braces 16, said interior being limited by the first radial braces 13, the second axial braces 14, and the second radial braces 15, in the distal direction. The distal protrusion 17 perpendicularly meets the control wheel 4 installed in the retaining element 1. A spring element 7, which extends in the distal direction to the control wheel 4, is placed on the distal protrusion 17. In the exemplary embodiment, the proximal end region of the control wire tensioning element 3 has a proximal protrusion 35 extending in the proximal direction. The proximal protrusion 35 is seated on the placement ring 34. The proximal protrusion 35 takes up the distal end of the spring element 7. The spring element 7 is thus inserted between the proximal protrusion 35 and the distal protrusion 17 with pretension. In other words, the spring element 7 pretensions the assembly comprising the control wheel 4 and control wire tensioning element 3 in the distal direction.

On the proximal side of the retaining element 1, a ring element is formed as an eyelet 5 in the region of the proximal ends of the axial end braces 16. The eyelet 5 is retained by the axial end braces 16. The eyelet 5 protrudes from the retaining element 1 in the proximal direction. The inner diameter of the eyelet 5 has a size which enables insertion of a finger or thumb of a user.

Function

The user can insert a finger or thumb into the eyelet 5. The retaining element 1 of the control element 100 is thereby securely retained. The user can place another finger (or the thumb if it is free) on the knurling 42 of the control wheel 4 and rotate the control wheel 4 about its axis.

In order to pull the control wire 2 in the proximal direction, the control wheel 4 is rotated such that the control wire tensioning element 3 moves in the proximal direction. The control wire tensioning element 3 is "screwed into" the control wheel 4 so to speak.

Because the control wheel 4 is tensioned via the control wire tensioning element 3 in the distal direction by means of the spring element 7, the control wire tensioning element 3 moves in the proximal direction relative to the control wheel 4, and the control wheel 4 still lies on the braces 13. Thus, the control wire tensioning element 3 moves in the distal direction guided on the rails 11. The control wire 2 is thereby pulled in the proximal direction.

The rotational movement of the control wheel 4 enables a very finely controllable movement of the control wire 2 in the longitudinal direction.

Further Alternatives

In the exemplary embodiment, the displacement force application device is designed as a control wheel 4 with an inner thread 41.

In one alternative, the displacement force application device may be designed as an electric motor or as a piezo element. The electric motor or the piezo element is mounted in the retainer 1 and mechanically connected to the control wire tensioning element 3 in order to apply a rotational force onto the control wire tensioning element 3. The control of the electric motor or of the piezo element may be a fine control, in which an extraordinarily slight movement of the control wire 2 can be created in the longitudinal direction of the wire. Thus, an especially sensitive fine control is possible.

In the exemplary embodiment, the control element 100 is coupled to the endoscope A via a screw connection B. The invention is not limited thereto. Any sort of coupling of the control element 100 to the endoscope A can be used such as, for example, a plug connection, a Luer-Lock connection, etc.

In the exemplary embodiment, the wire guide element 6 extends away from the endoscope A in the proximal direction. In one alternative, the wire guide element 6 may extend away from the endoscope A in the distal direction, provided it is advantageous for certain applications.

The wire guide element 6 may be omitted. If the wire guide element 6 is omitted, the control element 100 may be arranged closer to the endoscope A, which ensures a compact size.

The adapter D may be omitted.

Second Exemplary Embodiment

A second exemplary embodiment of the present invention is described with reference to FIGS. 10 to 15 in the following.

Figure 10:
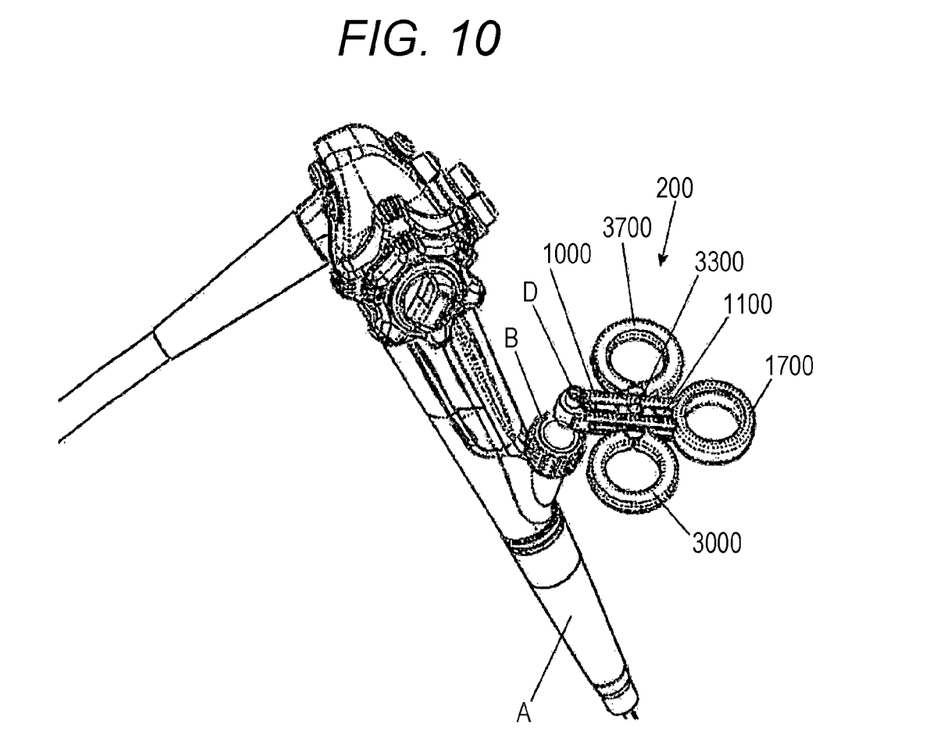
FIG. 10 shows a schematic perspective view of a control element, connected to an endoscope, of a second exemplary embodiment of the present invention.

A control element 200 according to the invention is coupled to an endoscope A, e.g. via a connection element B with a screw connection, which is provided on the endoscope A at the connection location of the control element 200. The connection location of the control element 200 on the endoscope A may be situated, as in the exemplary embodiment, on the control body of the endoscope A, but is not limited thereto.

To this end, the control element 200 is used to tension and to relax a control wire 2000 in the longitudinal direction of the wire in order to control a working element, which is provided on the distal side of the control wire 2000.

Merely as an example, the control element 200 may be used with a flexible endoscope A having a bending section. In this case, the control wire 2000 is anchored on the distal end of the bending section such that the anchoring location is spaced apart from the center line of the endoscope tube. The control wire 2000 extends through the bending section to a control element 200 arranged on the proximal side of the endoscope A. The bending section is thus actuated from the proximal side by the control element 200. Due to actuation of the control element 200, the control wire 2000 is tensioned, whereby the bending section is bent.

The precise structure and function of the control element 200 are described in the following.

The control element 200 has a housing element 1000. The housing element 1000 extends from the connection element B on the endoscope A in a direction pointing toward the user. In other words, the housing element 1000 extends away from the connection element B in a proximal direction. The connection element B is designed as a tube. The control wire 2000 is guided in the connection element B. The connection element B has, at a suitable location, a wire outlet opening, at which the control wire 2000 can exit the connection element B, e.g. laterally or alternatively (not shown) in the axial direction of the connection element B to the housing element 1000 (the wire outlet opening is not shown in the figures). In the region of the wire outlet opening, the control element 200 extends away from the connection element B at an approximately right angle with respect to the tube of the connection element B.

The connection element B further functions as a spacing element in order to suitably space the control element 200 apart from the endoscope A. This can improve the handling of the control element 200, because it is easier to grasp the control element 200 without elements of the endoscope A being in the way.

The control wire 2000 extends, in the interior of the connection element B, to the control element 200 in the proximal direction such that it changes its direction, i.e. is bent. The connection element B with the wire outlet opening thereby acts as an angled guide, on which the control wire 2000 is guided to the control element 200 such that it changes its direction.

An adapter D may be provided on the end of the connection element B opposite the connection; see FIG. 10. Further devices usable on the endoscope A may be connected on the adapter D as needed, such as a baby scope, a micro-tool connection, a rinsing connection for rinsing water, a suction connection for suctioning of fluids, etc.

The housing element 1000 of the control element 200 forms an axial-symmetrical frame element, as is shown in FIGS. 11 to 15. More precisely, the housing element 1000 is arranged in a mirror image about its axis of longitudinal extension. The housing element 1000 is formed by two parallel axial braces, which extend in the proximal direction from the region of the connection element B and which form an intermediate space between them with a predefined distance. A ring section 1700 is formed as an eyelet on the proximal side of the two parallel axial braces of the housing element 1000.

Figure 12:
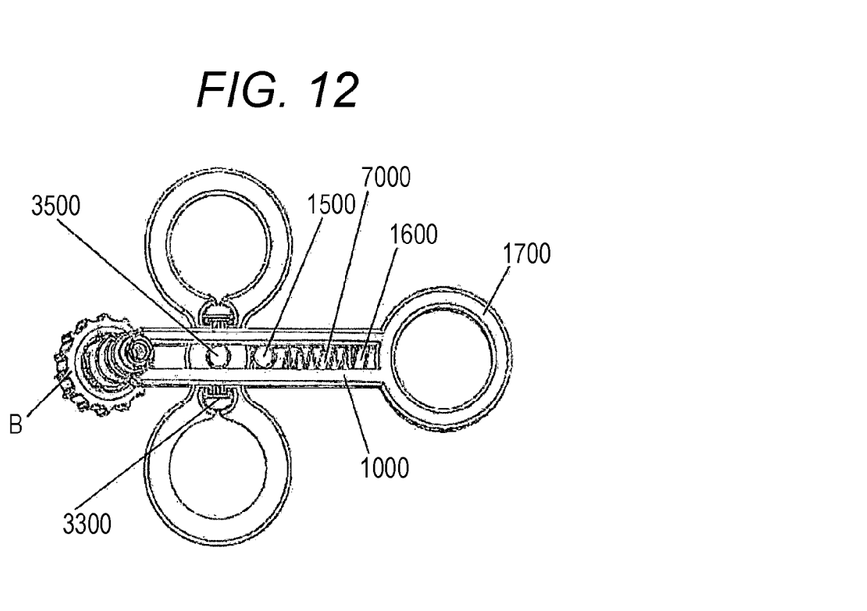
FIG. 12 shows a schematic perspective view of the control element 200 from FIG. 10 from below.
Figure 13:
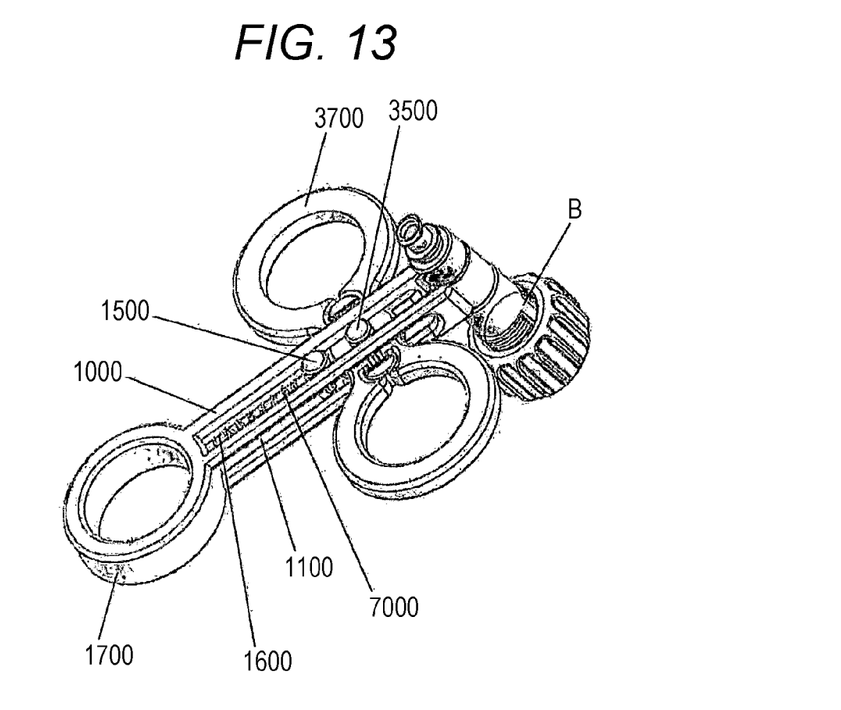
FIG. 13 shows a further schematic perspective view of the control element 200 from FIG. 10 from below.
Figure 14:
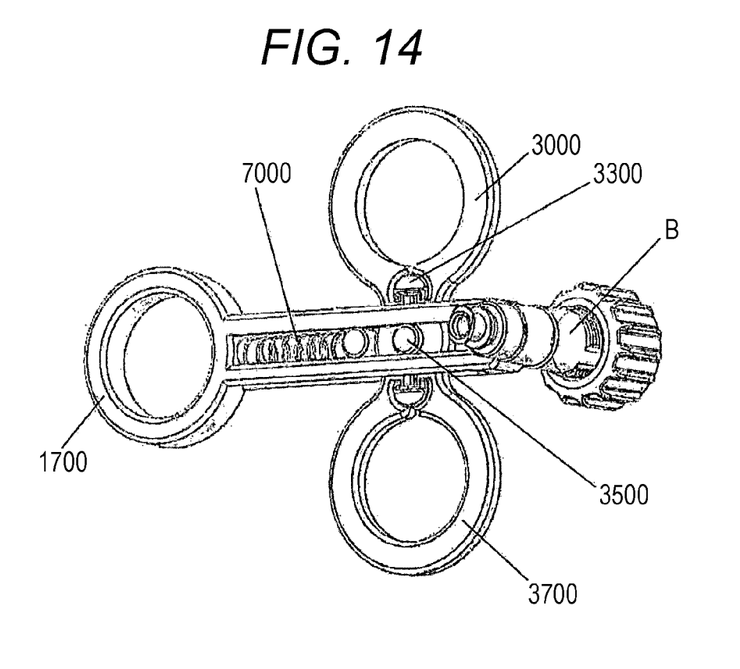
FIG. 14 shows a further schematic perspective view of the control element 200 from FIG. 10 from below.
Figure 15:
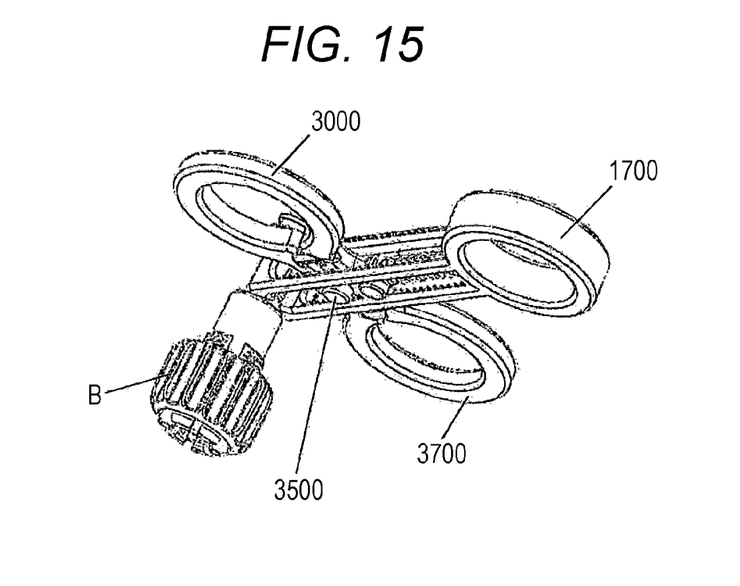
FIG. 15 shows a schematic perspective view of the control element 200 from FIG. 10 from above.

As is shown in FIG. 12, each of the two parallel axial braces of the housing element 1000 is provided such that an opening formed in the longitudinal extension is formed as a guide 1100. The two guides 1100 extend from the region of the connection element B in the proximal direction to the ring section 1700 and are structurally identical and parallel to one another. The guide 1100 is used to guide a lever element 3000 as described in the following.

The respective inner surfaces of the two parallel axial braces of the housing element 1000 form surfaces for guiding a pivot point element of the lever element 3000 as described in the following.

The housing element 1000 may be produced from plastic or metal.

The two guides 1100 guide a lever element 3000, which functions as a control wire tensioning element. The lever element 3000 is a flat element in the shape of the number eight. The thickness (height in the direction pointing upward and downward) of the lever element 3000 is dimensioned such that the lever element 3000 can slide in the guide 1100 in the longitudinal direction of the housing element 1000. For example, the thickness (height in the direction pointing upward and downward) of the lever element 3000 can be slightly less than the width (height in the direction pointing upward and downward) of the guide 1100.

The two openings of the eight of the lever element 3000 each form a ring section 3700. In the central region of the lever element 3000, a pivot point element 3500, which protrudes toward both sides (upward and downward), is designed in the form of a cylindrical pin. The outer diameter of this pivot point element 3500 is dimensioned such that the pivot point element 3500 can slide in the intermediate space between the respective inner surfaces of the two parallel axial braces of the housing element 1000 in the longitudinal direction of the housing element 1000. For example, the outer diameter of the pivot point element 3500 may be slightly less than the distance between the respective inner surfaces of the two parallel axial braces of the housing element 1000.

The control wire 2000 extends from the wire outlet opening of the connection element B into the inner region of the housing element 1000 to the lever element 3000 and is anchored on the lever element 3000.

More precisely, two control wires 2000 extend to an anchoring location 3300 on the lever element 3000. The anchoring location 3300 of the control wire is provided eccentrically to the displacement path of the lever element 3000 on the guide 1100 of the housing element 1000.

The anchoring location 3300 on the lever element 3000 is not specifically limited to a particular form. The respective anchoring location 3300 is formed on the lever element 3000, for example in the form of a pin element projecting toward the upper side, as is shown in the figures. The pin element may be formed through the formation of a groove enclosing the pin element (e.g. via laser).

Figure 11:
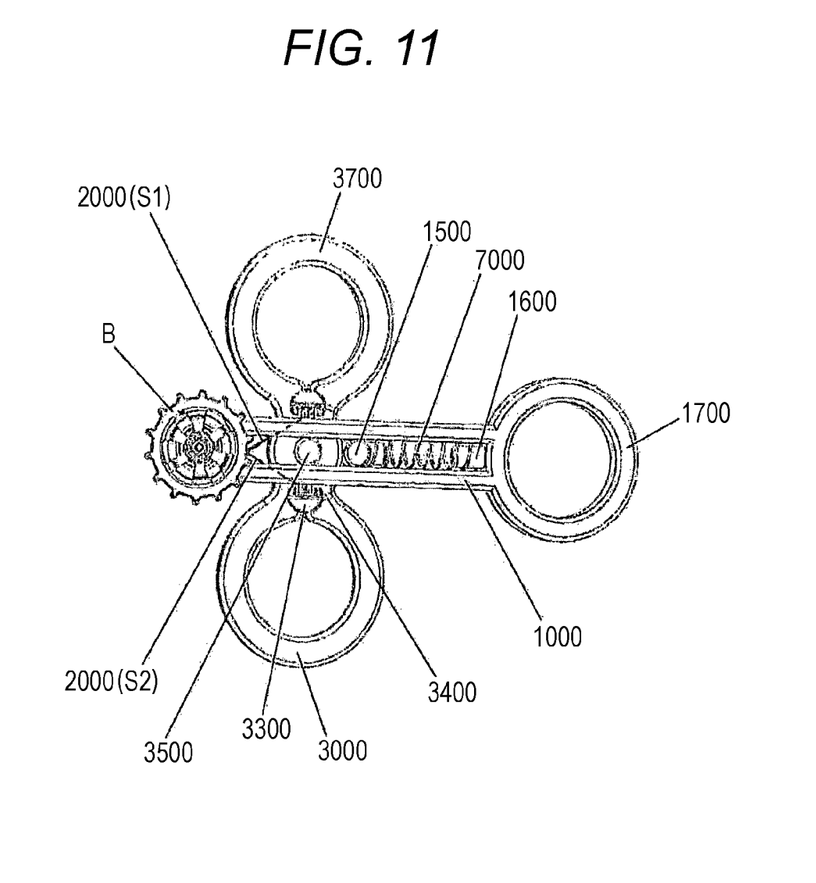
FIG. 11 shows a schematic top view of the control element 200 from FIG. 10.

As shown in FIG. 11, a first control wire S1 extends in the proximal direction to a first anchoring location 3300 (pin element shown at the top in FIG. 11). In the example of the pin element, the first control wire S1 is wound once about the axis of the pin element and exits the region of the anchoring location 3300 inserted in a small groove 3400 in order to be separated at the end of the groove 3400. The effective length of the control wire, i.e. the length up to the anchoring location 3300, can thereby be freely selected.

In a similar manner, a second control wire S2 extends in the proximal direction to a second anchoring location 3300 (pin element shown at the bottom in FIG. 11). In said example, the second control wire S2 is wound once about the axis of the second pin element and exits the region of the anchoring location 3300 inserted in a small groove 3400 in order to be separated at the end of the groove 3400.

Once the respective control wire 2000 (S1 or S2) has been inserted, the anchoring location 3300 and the groove 3400 can be sealed with a suitable sealant. Once the sealant has cured, the respective proximal end of the control wire 2000 is hidden in the anchoring location 3300 and the groove 3400.

In the housing element 1000, a protrusion 1600 protrudes into the interior of the housing element 1000 on the outer circumference of the ring section 1700 between the two axial braces of the housing element 1000 in the distal direction; see FIGS. 11 and 12.

A lever-loading element 1500 is provided on the distal side of the central region of the lever element 3000. Similar to the pivot point element 3500, the lever-loading element 1500 has a cylindrical pin element protruding toward both sides (upward and downward). The outer diameter of this pin element is dimensioned such that the pin element can slide in the intermediate space between the respective inner surfaces of the two parallel axial braces of the housing element 1000 in the longitudinal direction of the housing element 1000. For example, the outer diameter of the pin element may be slightly less than the distance between the respective inner surfaces of the two parallel axial braces of the housing element 1000. On the lever-loading element 1500, a protrusion protrudes into the interior of the housing element 1000 between the two axial braces of the housing element 1000 in the proximal direction.

A spring 7000 is arranged between the protrusion of the lever-loading element 1500 and the protrusion 1600. The spring 7000 tensions the lever element 3000 such that the spring 7000 is compressed during pulling of the lever element 3000 toward the ring section 1700. The spring element 7000 is thus inserted between the lever element 3000 and the ring section 1700. In other words, the spring element 7000 pretensions the lever element 3000 in the distal direction.

The length and stiffness of the spring 7000 are selected such that the lever element 3000 is in a distal position in the housing element 1000, in the standby position shown in FIGS. 11 and 12, and can be pulled to the ring section 1700 in the proximal direction.

The inner diameter of the ring section 1700 has a size which enables insertion of a finger, ideally of the thumb, of a user. The inner diameter of the respective ring section 3700 has a size which enables insertion of a finger, ideally of the index finger and of the middle finger, of a user.

Function

The user can insert the thumb into the ring section 1700. The housing element 1000 of the control element 200 is thereby securely retained. The index finger of the user is inserted into the one ring section 3700, and the middle finger of the user is inserted into the other ring section 3700.

In order to pull the two control wires 2000 (S1 and S2) in the proximal direction, the lever element 3000 is pulled to the ring section 1700 by the index finger and the middle finger. Pulling takes place opposite the spring force of the spring 7000 during this pulling process. Thus, the pulling process of the control wires 2000 (S1 and S2) takes place with increasing resistance of the spring 7000. Thus, the user has the sensation of more strongly tensioning the control wires 2000 (S1 and S2) as the spring resistance increases.

Furthermore, the user can tension one of the two control wires 2000 (S1 and S2) and relax the other of the two control wires 2000 (S1 and S2) by rotating the lever element 3000 about the pivot point element 3500.

Both functions are implemented by the same control element 200.

The rotational movement about the pivot point element 3500 in the center of the lever element 3000, combined with the possibility of pulling the lever element 3000 in the longitudinal direction, enables a very finely controllable targeted tensioning or relaxing movement of a selected control wire 2000.

Further Alternatives

In the exemplary embodiment, the lever element 3000 is always freely movable in the housing element 1000 of the control element 200 and is moved as desired by the user.

In one alternative, the pivot point element 3500 may have a central longitudinal hole or blind hole provided with an inner thread. A suitable screw can be screwed into this hole, with the head of said screw overlapping with the respective surface of the respective axial brace of the housing element 1000. By means of tightening this screw, the head can be clamped on the axial braces of the housing element 1000, whereby the lever element 3000 can be stopped in a position in the longitudinal direction of the housing element 1000 selected specifically by the user. The lever element 3000 can thereby be stopped at a specific location in the longitudinal direction of the housing element 1000 and stopped while rotated at a specific angle about the pivot point element 3500 relative to the housing element 1000.

In the exemplary embodiment, the control element 200 is coupled to the endoscope A via a screw connection B. The invention is not limited thereto. Any sort of coupling of the control element 200 to the endoscope A can be used such as, for example, a plug connection, a Luer-Lock connection, etc.

In the exemplary embodiment, the anchoring location 3300 is formed on the lever element 3000 in the form of a protruding pin element, which protrudes from a recess such that the control wire is wound about the pin element between the outer circumferential surface of the protruding pin element and the inner circumferential surface of the recess, and then the proximal end of the control wire is separated. Alternatively, the recess may be formed without a protruding pin element and have an inner circumferential form that corresponds to the outer circumferential form of a wire nipple. The proximal end of the control wire may be provided with the wire nipple. The wire nipple is inserted into said recess. In this alternative, the effective length of the control wire, i.e. the length up to the anchoring location 3300, is predefined.

In the exemplary embodiment, the connection element B extends away from the endoscope A in the proximal direction (sloping upward in FIG. 10). In one alternative, the wire guide element 6000 may extend away from the endoscope A in the distal direction (sloping downward in FIG. 10), provided it is advantageous for certain applications.

The connection element B can be shortened. If the connection element B is shortened, the control element 200 may be arranged closer to the endoscope A, which ensures a compact size.

The adapter D may be omitted.

One of the two control wires 2000 (S1 and S2) may be omitted. In this alternative, the proximal end of the one control wire 2 still available is mounted eccentrically with respect to the displacement path of the lever element 3000.

As shown in the exemplary embodiment, the lever element 3000 may have two anchoring locations 3300 for each control wire, wherein the two anchoring locations 3300, however, are spaced apart, at an unequal distance to one another, from the displacement path of the lever element 3000 on the guide 1100 of the housing element 1000. Thus, the two control wires 2000 (S1 and S2) are simultaneously tensioned and/or relaxed by means of a single movement of the lever element 3000, wherein the strength of the tensioning of the one wire and the strength of the relaxing of the other wire in this case are different.

The invention can advantageously be used with a gastroscope, a colonoscope, or a similar endoscope. The principle of the invention can be applied as well to any other type of endoscope. Although the invention is especially well-suited for flexible endoscopes, it can also be used with rigid endoscopes.

REFERENCE SIGNS LIST

1 Retainer
2 Control wire
3 Control wire tensioning element
4 Displacement force application device, control wheel
5 Eyelet
6 Wire guide element
7 Spring element
10 Connection element
11 Rail
12 First axial braces
13 First radial braces
14 Second axial braces
15 Second radial braces
16 Axial end braces
17 Distal protrusion
31 Groove
32 Outer thread
33 Hole
34 Placement ring
35 Proximal protrusion
41 Inner thread
42 Knurling
100 Control element
A Endoscope
B Screw connection, connection on the endoscope D Adapter
200 Control element
1000 Housing element
2000 Control wire
3000 Lever element
7000 Spring element
1100 Guide
1500 Lever-loading element
1600 Protrusion
1700 Ring section, eyelet
3300 Anchoring location of the control wire, pin element
3400 Groove for proximal end of the traction cable
3500 Pivot point element
3700 Ring section

The invention claimed is:

1. A control element for an endoscopic device, having
a frame;
a control wire, which can be moved back and forth in the longitudinal direction of the wire, for controlling the endoscopic device;
a control wire tensioning screw comprising:
  a cavity, wherein the control wire is mounted in the cavity;
  external threading; and
  a longitudinally-extending outer groove configured to slidably engage an inwardly-extending protrusion of the frame such that the control wire tensioning screw is guided within the frame; and
a displacement force actuator housed within the frame and having internal threading that threadedly engages the external threading of the control wire tensioning screw such that the control wire tensioning screw can be moved relative to the frame and the displacement force actuator, in order to effect adjustment of the control wire.

2. The control element for an endoscopic device according to claim 1, wherein
the protrusion of the frame comprises a rail; and
the control wire tensioning screw is displaceable along the frame due to engagement of the rail in the groove.

3. The control element for an endoscopic device according to claim 1, wherein
the displacement force comprises a control wheel comprising the internal threading.

4. The control element for an endoscopic device according to claim 3, wherein
the control wheel has knurling on the outer circumferential surface.

5. The control element for an endoscopic device according to claim 1, wherein
the displacement force application device is designed as an electric motor or as a piezo element.

6. The control element for an endoscopic device according to claim 1, wherein
a control wire nipple for the at least one control wire is mounted in the cavity.

7. The control element for an endoscopic device according to claim 1, wherein
an eyelet is formed on the proximal side of the frame, into said eyelet a finger or thumb can be inserted.

8. The control element for an endoscopic device according to claim 1, wherein
a proximal end of the control wire is mounted in the control wire tensioning screw.

9. The control element for an endoscopic device according to claim 1, further comprising an angled wire guide, on which the control wire is guided such that the wire guide changes the direction of the control wire.

10. An endoscopic device comprising a control element according to claim 1.

11. The control element for an endoscopic device according to claim 1, wherein the longitudinally-extending outer groove extends through the external threading.

* * * * *